United States Patent [19]

Wada

[11] 4,259,015
[45] Mar. 31, 1981

[54] METHOD AND DEVICE FOR MEASURING FINE PARTICLES

[76] Inventor: Akiyoshi Wada, 11-4, Akasaka 8-chome, Minato-ku, Tokyo, Japan

[21] Appl. No.: 24,863

[22] Filed: Mar. 28, 1979

[51] Int. Cl.³ .............................................. G01N 15/02
[52] U.S. Cl. ..................................... 356/336; 250/574
[58] Field of Search ............... 356/336, 338, 340, 342, 356/345, 354, 335; 73/61R, 61.4, 432 PS; 250/574

[56] References Cited

U.S. PATENT DOCUMENTS 3,802,271  4/1974  Bertelson .......................... 73/61 R X

FOREIGN PATENT DOCUMENTS 205356  11/1967  U.S.S.R. ................................ 73/432 PS

Primary Examiner—John K. Corbin
Assistant Examiner—Bruce Y. Arnold
Attorney, Agent, or Firm—Oblon, Fisher, Spivak, McClelland & Maier

[57] ABSTRACT

A method and device for measuring fine particles is disclosed, wherein a cell containing a suspended solution of fine particles is imparted a displacement by pulse or vibration, and a physical quantity in proportion to sedimentation rate of the fine particles is determined by measuring the relative position between the cell and the fine particles, whereby the sedimentation characteristics of the fine particles can be found by analyzing the frequency of electric signals obtained through optically mixing the scattered light from both the wall face of the cell and the fine particles.

2 Claims, 12 Drawing Figures

METHOD AND DEVICE FOR MEASURING FINE PARTICLES

BACKGROUND

The present invention relates to a method and device for measuring fine particles in order to determine a physical quantity in proportion to sedimentation rate of the fine particles by measuring in time sequence the position of the fine particles to a cell at the time of imparting the displacement by pulse or vibration to both a suspended solution of the fine particles and the cell containing the above solution.

The objective in a conventional method for obtaining the hydrodynamic properties of particles suspended in a liquid medium is the measurement of the movement of the solvent-solution boundary either under a centrifugal force, in the case of sedimentation measurement, or under an electric force in the case of electrophoresis. Another approach also involves the measurement of the deformation of the boundary in the case of diffusion measurement. In any case, the observation must be carried out for a long time, several hours for instance, and any disturbances during this period are accumulated and produce undesirable effects in the final result.

Recently, the availability of coherent light by laser oscillation has made it possible to measure the relative displacement of particles with respect to the cell wall at frequent intervals by measuring the interference of the scattered light from particles and the cell wall. The interference of the scattered light gives rise to beatnotes in a square-law detector such as a photomultiplier, if these light beams have different frequencies. When light is scattered by a moving particle, it is frequency shifted by the Doppler effect. Therefore, the details of the relative movement can be obtained by analyzing the frequency spectrum of the output current from the photoelectric detector. This so-called optical beating device has already made possible rapid measurements of diffusion and electrophoresis.

This invention opens up a possibility for rapid measurement of sedimentation phenomena, especially by introducing a vibrational force field instead of a constant centrifugal force which requires a relatively large mechanical installation.

BRIEF DESCRIPTION OF THE DRAWINGS

(a) $\alpha = 2$, (b) $\alpha = 4$, and (c) $\alpha = 5$.

DESCRIPTION OF THE PREFERRED EMBODIMENT

Referring to the theoretical background of the present invention, description is first directed to the movement of particles in the accelerated medium. Consider an incompressible liquid in a cell where one particle having a mass m is suspended. The motion of the particle when the cell is forced to move by an external force can be expressed by the following equation, $$m\frac{d^2r}{dt^2} = -\zeta\left(\frac{dr}{dt} - \frac{dr_c}{dt}\right) + m_o\frac{d^2r_c}{dt^2}, \tag{1}$$

where $m_o$ is the mass of the liquid, the volume of which is equal to that of the particle, $\zeta$ is the frictional coefficient of the particle, $r$ is the particle position, and $\gamma_c$ is the position from a point C which is arbitrarily chosen in the cell. The thermal motion of the particle, which will be taken into consideration in a later statement, is neglected at present.

By Fourier transforming Eq.(1), we obtain $$R(\omega) = \frac{\zeta + im_o\omega}{\zeta + im\omega} R_c(\omega), \tag{2}$$

where R is the Fourier transform of r:

$$R(\omega) = \frac{1}{2\pi} \int_{-\infty}^{\infty} r(t)e^{-i\omega t}dt. \tag{3}$$

When an external force is applied to vibrate the cell with a frequency $\omega_o$ and an amplitude $a_o$, so that $$R_c(\omega) = a_o\delta(\omega - \omega_o), \quad a_o \equiv |a_o|, \tag{4a}$$

$$\gamma_c(t) = \gamma_{co} + a_o e^{i\omega t}, \tag{4b}$$

the motion of the particle in the time domain is, from Eqs.(2)–(4), $$r(t) = r_{pi} + a^* e^{i\omega_o t}, \tag{5a}$$

$$a^* = \frac{\zeta + im_o\omega_o}{\zeta + im\omega_o} a_o, \tag{5b}$$

where $r_{co}$ and $r_{pi}$ are radii from the center of vibration of the point and the particle. From Eqs.(4) and (5) we have, $$\gamma(t) - \gamma_c(t) = (\gamma_{pi} - \gamma_{co}) + (a^* - a_o)e^{i\omega_o t}. \tag{6}$$

The second term on the right hand side of the above equation expresses the relative motion of the particle with respect to the cell. From Eq.(5), $$a^* - a_o = -i\frac{(m - m_o)\omega_o}{\zeta + im\omega_o} a_o. \tag{7}$$

If we define z and $z_o$ as $$Z = -i(m - m_o)\omega_o/(\zeta + i m\omega_o) = Z_o e^{i\phi}, \quad (8)$$
$$Z_o \equiv |Z|$$

the amplitude, $z_o\alpha_o$, and phase, $\phi$, of the particle vibration, relative to that of the cell, are given by $$z_o = |m - m_o|\omega_o/\sqrt{\zeta^2 + m^2\omega_o^2} \quad (9a)$$

and $$\phi = \tan^{-1}[(\zeta/m\omega_o)\sin n(m_o - m)]. \quad (9b)$$

When the experimental condition is selected so as to give the condition $m\omega_o/\zeta \ll 1$, the amplitude and phase are $$z_o \approx |m - m_o|\omega_o/\zeta = |S|\omega_o, \quad (10a)$$

$$\phi \approx (\pi/z)\sin n(m_o - m) \quad (10b)$$

and $$\alpha^* - \alpha_o = -is\omega_o\alpha_o. \quad (10c)$$

These equations tell us that the difference in phase between the relative displacement of the particle with respect to the cell and that of the cell vibration is $\pi/2$, and in this special but easily realizable case the sedimentation coefficients are obtainable by measuring both the amplitude of the relative displacement of the particle with respect to the cell and the amplitude of the cell itself.

The effect of the diffusion or Brownian motion of the particle in the liquid is independent, at least in the first approximation, of the above mentioned forced vibrational movement so that the former effect can simply be superposed on the latter motion. Therefore, the diffusion phenomenon is taken into account by making rpi in Eq.(5) a time-dependent variable rpi(t) whose time course is produced solely by the diffusion effect. This means that the following equation holds instead of Eq.(5):

$$\gamma(t) = \gamma pi(t) + \alpha^* e^{i\omega_o t}. \quad (11)$$

An explanation will now be given how one can measure the movement of particles with the use of scattered light. There are two kinds of methods for it: one is a method of heterodyne detection, and the other one is of homodyne detection. As a first step, reference is made to the method of heterodyne detection.

A small displacement of the particle with respect to the liquid cell wall, produced by the forced oscillation of the liquid cell as described above, can be measured by observing the light-intensity fluctuation due to the interference between the scattered light from the particle and that from the cell wall. The time-autocorrelation function of the fluctuation of the photo-current due to the interference of the scattered lights from these two sources is $$C(\tau) \alpha \sum_j Re - Ej(t)Ej^*(t + T)Ec^*(t)Ec(t + T) >, \quad (12)$$

where Ej is the electric field of the scattered light from the jth particle and Ec that from the cell wall, respectively. The intensity of the scattered light from the cell wall is assumed to be fairly strong in the present case (about 5 times or more that from the particle,) and this scattered light works as a local oscillator light. In this case the measurement is made in the heterodyne detection mode. By the use of the scattering vector K which is defined by $K \equiv k_s - k_o$, where $k_o$ and $k_s$ are the wave vectors of the incident and scattered light, respectively, Eq. (12) can be written in terms of the position of the particle, $r_j(t)$ and that of the cell $r_c(t)$:

$$C(T)\alpha Ac \sum_j AjRe < \exp(ik \cdot \{[Yj(t + \tau) - Yc(t + \tau)] - \quad (13)$$
$$[Yj(t) - Yc(t)]\}>,$$

where Aj and Ac are the intensity of the light from the particle and that from the local oscillator, and $< >$ indicates the ensemble average.

From Eqs.(6)–(8), and (11), we have $$[Yj(t + \tau) - Yc(t + \tau)] - [Yj(t) - Yc(t)] = \quad (14)$$
$$[Ypi,j(t + \tau) - Ypi,j(t)] + aj\{\cos[\omega_o(t + \tau) + \phi j] - \cos(\omega_o t + \phi j)\},$$

where $$aj \equiv z_o,j\alpha_o, \quad (15a)$$

$$aj = |aj| = z_o,j\alpha_o, \quad (15b)$$

and rpi,j(t) is the center of vibration of the jth particle. From Eqs. (13) and (14), and by considering the diffusion equation, we have $$< \exp(iK \cdot \{[rj(t + \tau) - rc(t + \tau)] - [rj(t) - rc(t)]\}) > \quad (16)$$
$$= \exp(iK \cdot [r_{pi,j}(t + \tau) - r_{pi,j}(t)])$$
$$X < \exp(iK \cdot aj \cdot \cos\{\omega_o(t + \tau) + \phi j\} - \cos(\omega_o t + \phi j)\}) >$$
$$= e^{-Djk2|\tau|}Jo(|2K \cdot aj \sin(\omega_o\tau/2)|),$$

where Dj is the diffusion coefficient of the jth particle, and Jo(x) is the Bessel function of the 0th order. The auto-correlation function is given from the above equation and Eq.(13) as $$C(\tau)\alpha Ac \sum_j Aje^{-DjK2|\tau|}Jo(|2K \cdot aj \sin(\omega_o\tau/2)|). \quad (17)$$

When, $2K.a \leq 1$, that is, $x \lesssim 1$, the Bessel function can be expanded as $$Jo(x) = 1 - (x^2/4) + (x^4/64) - \ldots$$

and $$C(\tau)\alpha Ac \sum_j Aje^{-DjK2|\tau|}[1 - (K \cdot aj)^2\sin^2(\omega_o\tau/2)] = \quad (18)$$
$$Ac \sum_j Aje^{-DjK2|\tau|}\{1 - (K \cdot aj)^2/2) +$$
$$[(K \cdot aj)^2/2]\cos(\omega_o\tau)\}.$$

The power spectrum of the photocurrent is given by the Fourier transform of the auto-correlation function, C(J); we have from Eq.(18), under the condition of $2K.a \leq 1$, $$I(\omega)\alpha Ac \sum_j Aj\{[1 - (K \cdot aj)^2/2]LDjK^2(\omega) + \quad (19)$$
$$[(K \cdot aj)^2/2]LDjK^2(\omega - \omega_o)\},$$

where $L_1(\omega - \omega_o)$ is the Lorentzian function of the half power frequency and center frequency $\omega_o$.

Since the values of K and $\omega_o$ and the direction of the vibration are known, the amplitude of the relative displacement of the jth particle $aj$ can be determined by comparing the experimental auto-correlation function with the theoretical one given by Eq. (17). From the value of $\alpha j$ together with the value of the amplitude of the cell $\alpha o$ we can obtain $Z_{o,j}$ and then $|sj|$ by Eq. (15). In the special case of a small amplitude, the auto-correlation function consists of an exponentially decreasing function, which comes from the diffusion effect, with a sinusoidal-like function superposed. The latter function is due to the sedimentation. If an experiment is performed under the condition $DK^2 \sim \omega o$, the sedimentation effect appears as a ripple on an exponentially decaying curve; hence $\alpha j$ can be obtained simply from the amplitude of the ripple mentioned above. On the other hand, the power spectrum $I(\omega)$ shows two Lorentzian curves centered at $\omega=0$ and $\omega=\omega o$, respectively, where the value of $\alpha j$ is calculated from the ratio of the heights of these two peaks. In any case, from Eqs. (18) and (19), the average sedimentation coefficient is given by $$(\bar{S}^2)^{\frac{1}{2}} = (1/\omega_o)(\sum_j A j \alpha j^2 / a_o^2 \sum_j A j)^{\frac{1}{2}}. \quad (20)$$

It is from the above equation that the measured sedimentation coefficient is seen to be the root means square average of the sedimentation coefficient of each particle when the particle size is heterogeneous.

On the other hand, the diffusion coefficient is obtainable from the exponentially decaying curve, given as the upper envelope of the ripple [Eq. (18)], or by carrying out another experiment without vibrating the sample cell.

Now the method of homodyne detection is touched upon. The measurement in the homodyne detection mode is achieved by removing the local oscillator light and by detecting the interference among the scattered light from different particles in the solution. Therefore, by summing up the interferences between the light scattered from all pairs of particles, we obtain the homodyne correlation function.

$$C(\tau) \alpha \sum_{j \neq k} < E j(t) E j^*(t+\tau) E k^*(t) E k(t+\tau) > \quad (21)$$
$$\alpha \sum_{j \neq k} A j A k < \exp(i K \cdot \{[Y j(t+\tau) - r k(t+\tau)] - [r j(t) - r k(t)]\} >,$$

where the suffixes denote the particles. By a similar procedure to the one used to obtain Eq. (16) with Eq.(14), Eq. (21) is changed to $$C(\tau) \alpha \sum_{j \neq k} A j A k e^{-(Dj-Dk)K^2 \tau} J_o(|2K \cdot a_{jk} \cdot \sin(\omega_o \tau/z)|). \quad (22)$$

When the amplitude is small, the equivalent equation for Eq. (18) is, $$C(\tau) \alpha \sum_{j \neq k} A j A k e^{-(Dj-Dk)K^2 \tau} \{[1 - (K \cdot a_{jk})^2/2] + [(K \cdot a_{jk})^2/2]\cos(\omega_o \tau)\}, \quad (23)$$

where $\alpha jk$ is the amplitude of the vibration of the jth particle with respect to kth particle. When $m\omega o/\zeta \leq 1$, from Eqs. (10) and (15) we have a relation $$ajk = aj^* - ak^* = Sj - Sk \cdot \omega o a o. \quad (24)$$

A value $(\sum_{j \neq k} A j A k (Sj-Sk)^2)/(\sum_{j \neq k} A j A k)$ is found, from Eqs. (23) and (24), to be obtainable from the homodyne experiment, which is transformed to the standard deviation of the distribution of the sedimentation coefficients of particles, $\delta$, as follows:

$$\frac{\sum_{j \neq k} A j A k (Sj-Sk)^2}{\sum_{j \neq k} A j A k} = \frac{2 \sum_j A j (Sj-\bar{S})^2}{\sum_j A j (1 - \sum_j A j^2/(\sum_j A j)^2)} = z \delta^2, \quad (25)$$

where $\bar{S}=(\Sigma j A j S j/\Sigma j A j)$.

Figure 1:
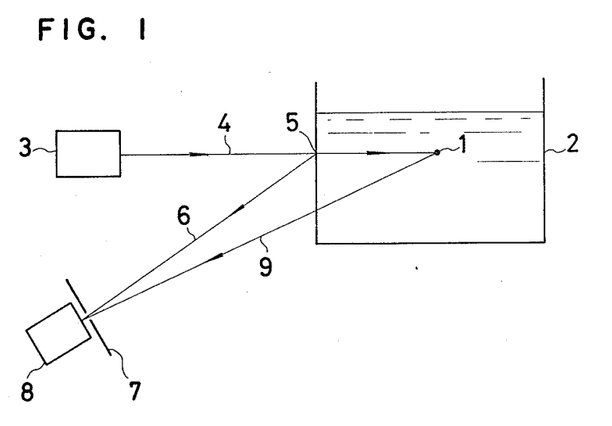
FIG. 1 is a block diagram, visualizing the concept of the present invention.
Figure 2:
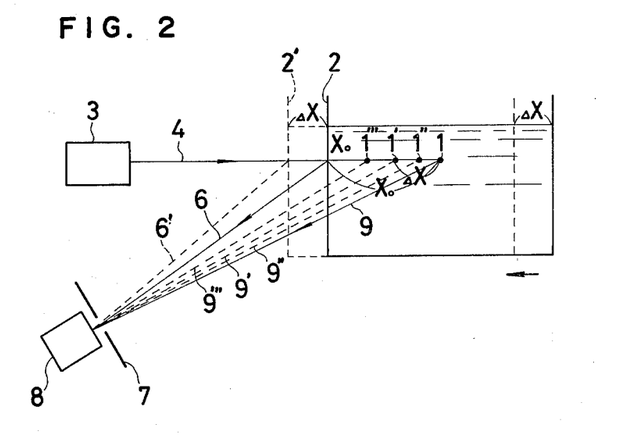
FIG. 2 and FIG. 3 each are block diagrams for describing the several states when the liquid cell has been shifted in the different directions of the arrows, respectively.

The method according to the present invention based on the above-described theory will now be described with reference to FIGS. 1–3.

For a start, a fine particle 1, as material to be measured, is made to disperse within a liquid cell 2. At a short distance from the liquid cell 2 is placed a source of laser light 3, from which a light beam 4 is irradiated to the liquid cell 2. This light beam 4 strikes first on the wall face 5 of the liquid cell 2 and is then partly scattered. A portion of this scattered light 6 passes through a pin-hole 7 into a photoelectric converter 8. On the other hand, a portion of the light 9 scattered by the fine particle 1 passes through the pin-hole 7 into photoelectric converter 8. In such a way, there occurs the optical heterodyne mixing (interference) between the two scattered lights.

Next, with reference to FIG. 2, description will be made on the correlation of signal output by the optical heterodyne mixing to the sedimentation characteristics of the fine particles. Let the distance from the wall face 5 of the liquid cell 2 to the fine particle 1 to be Xo, and assume the liquid cell 2 is displayed by $\Delta x$ in the direction of the light source 3 up to the position 2' by an outside force. In the case where the density of fine particles 1 is equivalent to that of the solution, the relative position of the wall face 5' to the fine particle 1' does not vary because the fine particle 1 also is displaced by $\Delta x$, in the direction of the light source 3 up to the position 1'. However, in the case where the density of fine particles 1 is higher than that of the solution, the particle is displaced to a lesser extent. Hence the position gets no further than the position 1''. On the contrary, in the case where the density of the particle 1 is lower than that of the solution, the particle is displaced to a large extent, i.e., the particle will come to a standstill at the position 1'''.

Figure 3:
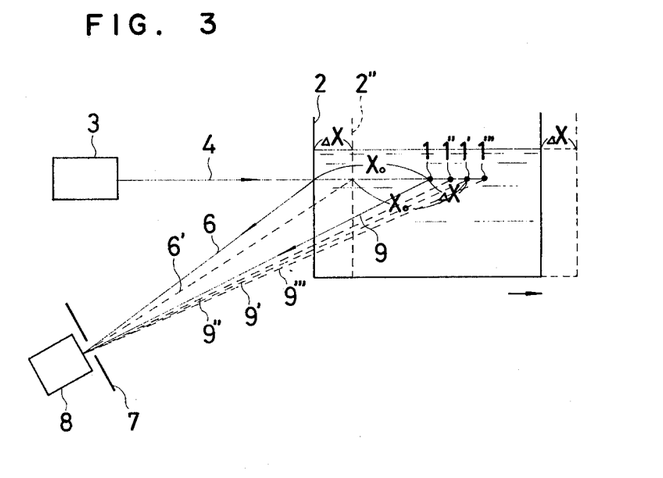

FIG. 3 shows the case where the liquid cell 2 is displaced by $\Delta x$ in the direction opposed to the light source 3 up to the position 2''. The displacement of the fine particle 1 here is the same as the displacement in FIG. 2.

In such an arrangement, when the liquid cell 2 is put in vibration from side to side, the difference in the amplitude and the phase of the particles as compared with that of the cell above reflected in the frequency characteristics of the electric signal obtained from the photoelectric converter 8 which receives both the scattered light 6 dispersed by the wall face 5 and the scattered light 9 coming from the fine particle 1. Consequently, it becomes possible to determine various kinds of sedimentation characteristics of fine particles through the investigation of the frequency characteristics of the electric signals.

An embodiment of the present invention and an experiment conducted therewith on the very device will be described hereinafter with reference to FIGS. 4 to 10.

Figure 4:
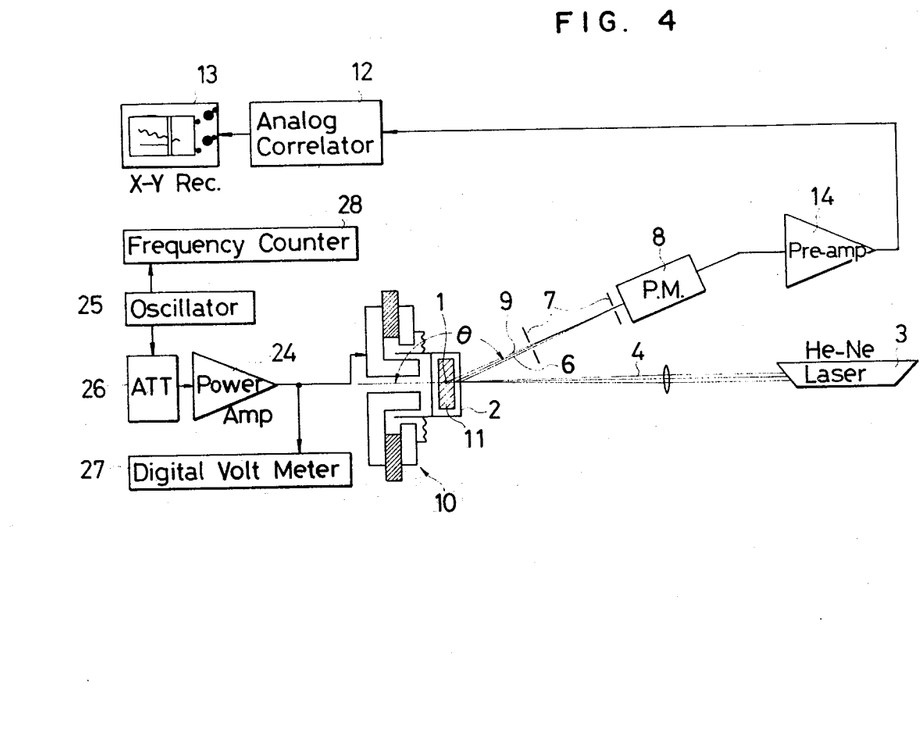
FIG. 4 is a block diagram, showing the arrangement of the electrical and optical elements according to the present invention.

The light source 3 is a helium-neon laser with 50 mW output power and 632.8 nm wavelength. The incident laser beam 4 emitted from the light source 3 passes into the cell 2 attached to the vibrator 10 and further into the sample 11 in the same cell 2. This sample 11 consists of polystyrene latex spheres suspended in water. The diameter of these spheres is 3.0 μm, and their density is measured to be 1.14±0.11. The incident laser beam 4 is received by the photomultiplier 8 while being divided into the light beam 6, scattered by a small scratch formed on the surface of the window 19 of the cell 2 and the light beam 9, scattered by spheres 1 in the sample 11. The output photoelectric current from the photomultiplier 8 is measured by a correlator 12 and is displayed by an X-Y recorder 13 through the medium of a preamplifier 14.

Figure 5:
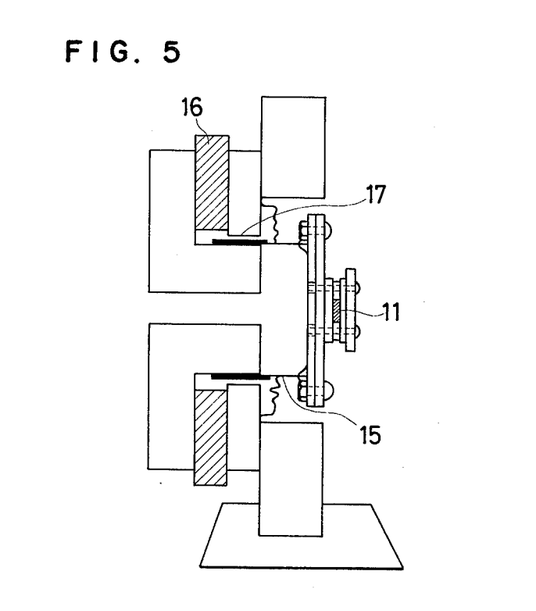
FIG. 5 shows details of a vibrator (side view).
Figure 6:
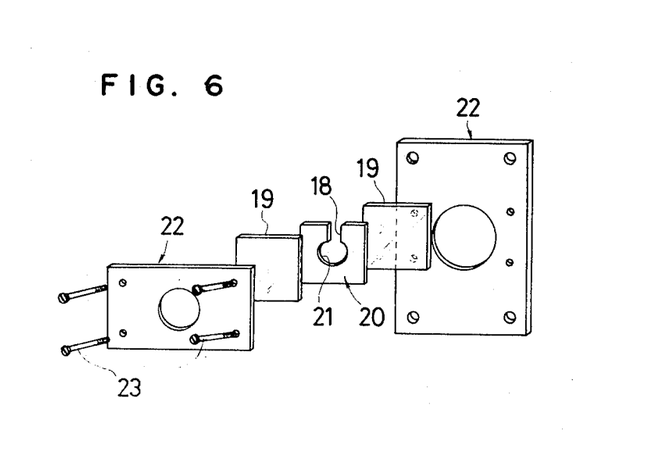
FIG. 6 is an exploded view of a cell mounting.
Figure 7:
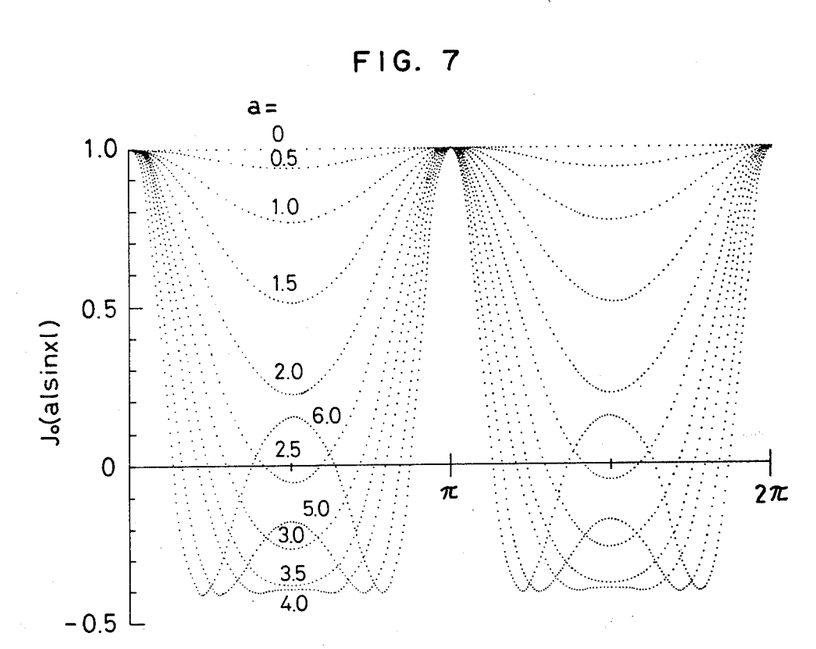
FIG. 7 shows the behavior of the Bessel function $J_o(\alpha | \sin \chi |)$ at several values of $\alpha$ against $\chi$.
Figure 8:
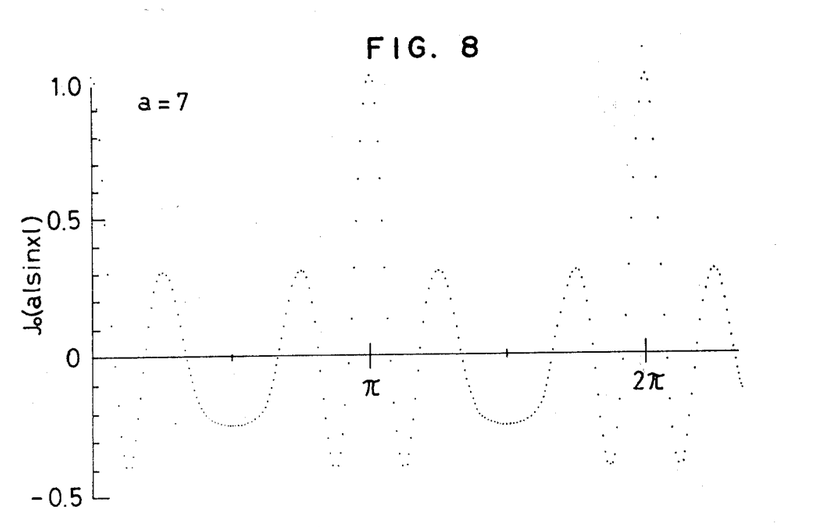
FIG. 8 shows a behavior of $J_o(\alpha | \sin \chi |)$ at high $\alpha$ value.

The vibrator 10 is obtained by modifying the mechanical part of a speaker which is commercially available. The sample 11 is put into the cell 2 which is fixedly secured with the use of an adhesive agent on the voice coil bobbin 15. The assembly is oscillated by the magnet 16 and voice coil 17. This cell 2 opens on its upside with a narrow inlet 18, and is placed within cell windows 19, which consists of plate glass on each side of silicon rubber plate 20 having a hollow part 21 in the central part thereof. Each side of the cell windows 19 are further put into two holders 22 which are clamped with screws 23.

The cell is designed to make its mass as small as possible. Also, to avoid the surface wave which is caused by the vibration and which may produce undesirable turbulence in the cell 2, the liquid surface is made small. To achieve this, a narrow inlet 18 is opened at the upper part of the cell 2. The diameter of the cell is 5 mm, and its depth 0.8 mm.

The cell 2 and the system are arranged so that the cell window 19 is vertical, and the incident laser beam 4 is perpendicular to it. A small scratch is made on a surface of window 19 to scatter the local oscillator light to carry out the heterodyne measurement. The absence of a bending vibrational mode which will diffract the light beam and produce a spurious signal due to an amplitude modulation in the scattered light, is carefully confirmed. In the present experiment, the scattering angle $\theta$ is chosen close to 180°.

The vibrator 10 is driven by a power amplifier 24 with a function generator. This power amplifier 24 is connected to an oscillator 25 via attenuator 26. The driving voltage and frequency are monitored by a digital voltmeter 27 and a frequency counter 28 connected to the frequency of the oscillator 25. The oscillation is monitored using to the frequency counter 28.

The amplitude of the vibration is measured by the output voltage of an electromechanical transducer, not shown in the figure, attached to the cell 2.

Now, description is directed to the experiment conducted on the above-mentioned device at a room temperature of 23° ±10° C. and on the basis of the previously-stated experimental condition. To show results of the theoretical calculation, the second term of Eq. 16, $J_0(\alpha|\sin|)$, which gives the contribution of the sedimentation effect, is plotted against $x = \omega_0 t/z$ for several values of $\alpha = 2K.\alpha$ in FIG. 7. When the scattering angle is chosen close to 180° C., as is the case in the present experiment, $\alpha = 8\pi(a/n\lambda)$, where n is the refractive index of the liquid, and λ the wave length of the incident light. In a region of small amplitude, $\alpha < 1$, the plot is a sinusoidal curve with period $\pi$. By increasing $\alpha$, new peaks appear at positions, $X = \pi/2, 3\pi/2, \ldots$ More peaks appear for higher values of $\alpha$ [FIG. 8]. These results are easily explained by a physical picture of the interference of scattered light. Namely, as the vibrational amplitude becomes larger, the displacement of the particle relative to the cell wall extends beyond several wave lengths of the incident light. Then the scattered light from the particle and that from the cell wall interfere with each other several times during one period of vibration. This interference appears as peaks within one period, $\zeta = \pi$, in the correlation profile.

Figure 9:
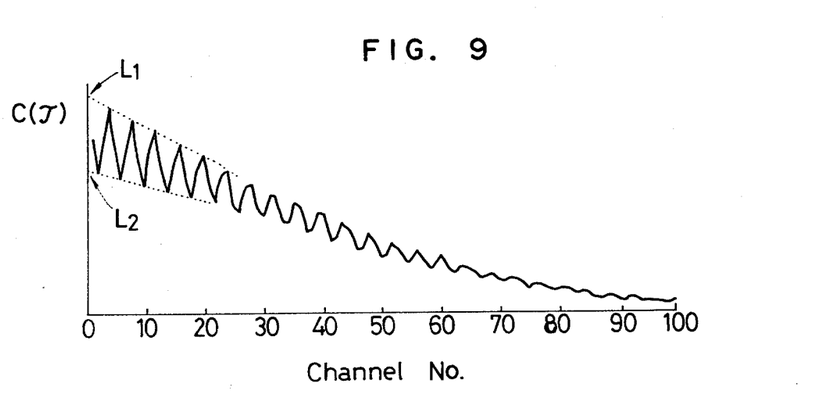
FIG. 9 is a typical time-autocorrelation function of scattered light by a polystyrene suspension in a vibrating cell ($\omega_o/2\pi = 125$ Hz) in the region $\alpha < |$. The time scale in the abscissa is 2 milliseconds/channel. The deformation of the profile comes from a discrete sampling by the autocorrelator, that is, 4 channels per period. $L_1$ and $L_2$ are the intercepts of the upper and lower envelopes of the profile, respectively.
Figure 10:
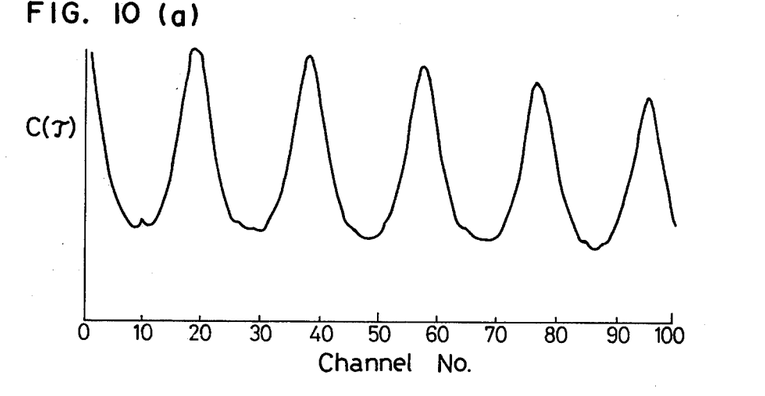
FIG. 10 shows the autocorrelation functions of scattered light by polystyrene suspension in a vibrating cell ($\omega_o/2\pi = 1$KHz) at higher values of $\alpha$.

These phenomena are clearly reproduced in the present experimental results. The photocurrent correlation function measured under the condition of small vibrational amplitude is shown in FIG. 9. The ripples appear on the exponentially decaying curve of the diffusion effect. It is also shown that the amplitude of the ripples increases with increasing vibrational amplitude. A magnified plot is shown in FIG. 10(a).

When the amplitude increases, new peaks appear between the original peaks with period $\pi$ as shown in FIGS. 10(b) and 10(c), just as predicted by the theory.

On the other hand, the polystyrene latex sphere, whose density is equal to that of the liquid, should not produce ripples. This is confirmed experimentally with such spheres by keeping the other conditions as similar as possible. Therefore, it is proved that the ripples observed in the previous experiment come from the sedimentation effect.

The sedimentation coefficient can be obtained either from the amplitude of the sinusoidal curve in the case of a small amplitude experiment or from the curve-fitting procedure for a large amplitude experiment. In the former case, from the values of the intercepts which are given by extrapolating the upper and lower envelopes of the sinusoidal curve to the ordinate axis, $L_1$ and $L_2$ as shown in FIG. 9, the value of $\alpha$ and therefore that of S can be obtained by the following equation:

$$S = (1/\omega_0 a_0)(L_1 - L_2)/L_1. \tag{26}$$

On the other hand, when the amplitude of the vibration is large enough to produce additional peaks within one period of vibration, a curve-fitting method is applicable to evaluate the sedimentation coefficient. A comparison over the whole profile or the measurement of the particular $a_0$ value at which a new peak just appears (FIG. 10), may be employed.

In the correlation measurement, it is useful to set the delay time per channel of the correlator equal to the inverse of the even multiples of the vibrational frequency of the cell so that the channels receive data at the maximum and minimum points of the correlation function.

In the present experiment, the sedimentation coefficients obtained with these two different methods agreed well to give $S = 3.0 \times 10^{-7}$ as compared with the expected value $s = 2.81 \times 10^{-7}$.

As is evident from the above-mentioned description, it is practicable to measure momentarily even the insignificant displacement of the particles to the wall face of the liquid cell. In other words, if according to the present invention, there is no necessity for sedimentating the particles up to the distance measurable with the eye or with the use of some optical instrument by imparting to the particle an acceleration in a definite direction for long hours, as is the case with the conventional measurement utilizing the field of gravity. Thereupon, it may be given as a conclusion that the present invention has an effect that makes it possible to make measurements in a very short time and with high accuracy, and further to make the measuring device into a small size, and so on.

What I claim is:

1. A method for determining the size distribution of fine particles suspended in a fluid comprising:

causing relative movement between said fine particles and a cell containing said fluid by applying an acceleration force to said cell by pulse or vibration; and then, determining a physical quantity which is proportional to the sedimentation rate of said fine particles through the measurement of the position and phase of said fine particles relative to said cell.

2. A device for determining the size distribution of fine particles suspended in a fluid comprising: a light source created by a laser; a means of applying displacement by pulse or vibration to a cell containing said suspended solution of fine particles; a photoelectric converter for optically mixing reference light coming from a wall face of said cell and scattered light propagated from said fine particles, and converting them photoelectrically; and a means for analyzing the frequency of electric signals obtained from said converter.

* * * * *